(12) United States Patent
Katase et al.

(10) Patent No.: US 9,440,050 B2
(45) Date of Patent: Sep. 13, 2016

(54) FLUID INFUSER

(71) Applicant: SEIKO EPSON CORPORATION, Tokyo (JP)

(72) Inventors: Makoto Katase, Azumino (JP); Yukihiro Uchiyama, Okaya (JP)

(73) Assignee: SEIKO EPSON CORPORATION, Tokyo (JP)

( * ) Notice: Subject to any disclaimer, the term of this patent is extended or adjusted under 35 U.S.C. 154(b) by 70 days.

(21) Appl. No.: 14/515,753

(22) Filed: Oct. 16, 2014

(65) Prior Publication Data
US 2015/0112268 A1 Apr. 23, 2015

(30) Foreign Application Priority Data

Oct. 23, 2013 (JP) ................. 2013-219894

(51) Int. Cl.
*A61M 25/06* (2006.01)
*A61M 5/142* (2006.01)
*A61M 5/32* (2006.01)

(52) U.S. Cl.
CPC ..... *A61M 25/0606* (2013.01); *A61M 5/14248* (2013.01); *A61M 5/329* (2013.01); *A61M 5/3287* (2013.01); *A61M 5/14228* (2013.01); *A61M 2005/14252* (2013.01)

(58) Field of Classification Search
CPC .............. A61M 25/0606; A61M 5/14248; A61M 5/3287; A61M 5/329; A61M 5/14228; A61M 2005/14252
USPC ............ 604/164.01–164.09, 165.01–165.04, 604/208–211, 264, 272–274
See application file for complete search history.

(56) References Cited

U.S. PATENT DOCUMENTS 5,846,226 A * 12/1998 Urmey .......................... 604/158
6,241,709 B1 * 6/2001 Bechtold et al. ............. 604/207

FOREIGN PATENT DOCUMENTS

JP 2001-245982 A 9/2001

OTHER PUBLICATIONS

WO 2013/132192, Roche et al., publication date: Sep. 2013.*

* cited by examiner

*Primary Examiner* — Manuel Mendez
(74) *Attorney, Agent, or Firm* — Maschoff Brennan (57) ABSTRACT

A fluid infuser includes an introduction needle having a projection on a peripheral surface, and an infusion tube configured to cover the introduction needle. The projection of the introduction needle is installed at a position where the introduction needle comes into contact with the infusion tube, and includes a first surface and a second surface. The first surface is arranged at a picking end side of the introduction needle with respect to the second surface, and an angle of inclination of the first surface is larger than an angle of inclination of the second surface. The fluid infuser is configured to guide an infusion tube to an object of insertion adequately, and allow the introduction needle to be pulled out easily from the infusion tube.

7 Claims, 10 Drawing Sheets

FLUID INFUSER

BACKGROUND

1. Technical Field

The present invention relates to a fluid infuser configured to infuse fluid into an object of fluid infusion such as a biological body.

2. Related Art

In order to transport drug solution from an administration pump to a subcutaneous structure, an infusion tube such as a catheter is inserted into and indwelt in the subcutaneous structure. Since the catheter is formed of a soft material which adapts to the subcutaneous structure. Therefore, in order to insert the catheter into the subcutaneous structure, the catheter covers a metallic needle, and is inserted simultaneously into the subcutaneous structure together with the metallic needle.

JP-A-2001-245982 discloses a double injection needle in which a metallic needle (inner needle) is covered with a catheter (soft jacket needle). The fact that projections are provided on a peripheral surface of the metallic needle and the projections are provided in a direction corresponding to a direction of insertion of a metallic needle is disclosed.

An infusion tube such as a catheter is inserted into and indwells only the infusion tube in the subcutaneous structure, the infusion tube needs to be guided adequately to the subcutaneous structure or the like. After the infusion tube has been guided, an introduction needle inserted together with the infusion tube needs to be pulled out from the infusion tube. In other words, a fluid infuser configured to guide the infusion tube adequately and to be easily pulled from the infusion tube is desired.

SUMMARY

An advantage of some aspects of the invention is to provide a fluid infuser configured to guide an infusion tube to an object of insertion adequately, and allow an introduction needle to be pulled out easily from the infusion tube.

An aspect of the invention is directed to a fluid infuser including: an introduction needle having a projection on a peripheral surface; and an infusion tube configured to cover the introduction needle, wherein the projection of the introduction needle is installed at a position where the introduction needle comes into contact with the infusion tube, and includes a first surface and a second surface, the first surface is arranged at a picking end side of the introduction needle with respect to the second surface, and an angle of inclination of the first surface is larger than an angle of inclination of the second surface.

BRIEF DESCRIPTION OF DRAWINGS

The invention will be described with reference to the accompanying drawings, wherein like numbers reference like elements.

DESCRIPTION OF EXEMPLARY EMBODIMENTS

According to the specification and the attached drawings, at least the followings become apparent. In other words, in a fluid infuser including an introduction needle having a projection on a peripheral surface, the introduction needle covered with an infusion tube, wherein the projection of the introduction needle is installed at a position where the introduction needle comes into contact with the infusion tube, the projection of the introduction needle includes a first surface and a second surface, an angle of inclination of the first surface is larger than an angle of inclination of the second surface, and the first surface is arranged on a picking end side of the introduction needle.

In this configuration, since the angle of inclination of the first surface of the projection of the introduction needle is set to be larger than the angle of inclination of the second surface, the first surface of the projection engages an inner peripheral surface of the infusion tube, and the introduction needle is inserted into the subcutaneous structure or the like and, simultaneously, the infusion tube can adequately be guided into the subcutaneous structure. The angle of inclination of the second surface of the projection of the introduction needle is smaller than the angle of inclination of the first surface. Therefore, a frictional force applied to the infusion tube when the introduction needle is pulled out may be reduced. Therefore, the introduction needle can be pulled from the infusion tube easily.

Preferably, the projection on the introduction needle is provided in a range where the infusion tube covers the introduction needle.

In this configuration, a portion of the introduction needle coming into contact with the subcutaneous structure is not provided with the projection, so that the introduction needle can be inserted smoothly into the subcutaneous structure or the like.

Preferably, a projection is provided on an outer peripheral surface of the infusion tube, the projection of the infusion tube includes a third surface and a fourth surface, an angle of inclination of the third surface is smaller than an angle of inclination of the fourth surface, and the third surface is arranged on an inlet port side of the infusion tube.

In this configuration, since the frictional force in the direction of insertion of the infusion tube which covers the introduction needle with respect to the subcutaneous structure or the like may be reduced, the infusion tube may be smoothly inserted into the subcutaneous structure. Since the frictional force of a pulling-out direction of the infusion tube with respect to the subcutaneous structure may be increased, the infusion tube may be prevented from being pulled out easily from the subcutaneous structure or the like. When pulling out the infusion tube from the subcutaneous structure or the like, the introduction needle is already pulled out from the infusion tube. Therefore, since the infusion tube itself is deformable inward by a resilient force of the infusion tube, the infusion tube may be pulled out without applying a burden on the biological body irrespective of the projection provided on an outer peripheral surface.

Preferably, the outer peripheral surface is provided with a groove extending in a longitudinal direction of the introduction needle in an outer periphery of the introduction needle.

In this configuration, a contact area of the introduction needle with the infusion tube is reduced and hence the frictional force of the introduction needle with respect to the infusion tube may be reduced. Therefore, the introduction needle can be pulled from the infusion tube easily.

Preferably, a material of the introduction needle is harder than the material of the infusion tube.

In this configuration, the infusion tube may be guided to the subcutaneous structure by using the hard introduction needle.

Preferably, a material of the introduction needle is a metal, and a material of the infusion tube is a resin.

In this configuration as well, the infusion tube may be guided to the subcutaneous structure by using the hard introduction needle.

Preferably, the angle of inclination of the first surface has at least an angle of 90 degrees.

In this configuration, the projection of the introduction needle easily engages an inner surface of the infusion tube, so that the projection of the introduction needle allows the infusion tube to be inserted into the subcutaneous structure or the like by supporting adequately from the inner surface of the infusion tube.

Preferably, an outer peripheral length of the infusion tube on the inlet port side is shorter than an outer peripheral length of the infusion tube on the other end side.

In this configuration, the inlet port side of the infusion tube may be formed into a tapered shape which is thinner than a center portion, so that the infusion tube is allowed to be picked easily into the subcutaneous structure or the like.

First Embodiment

Figure 1:
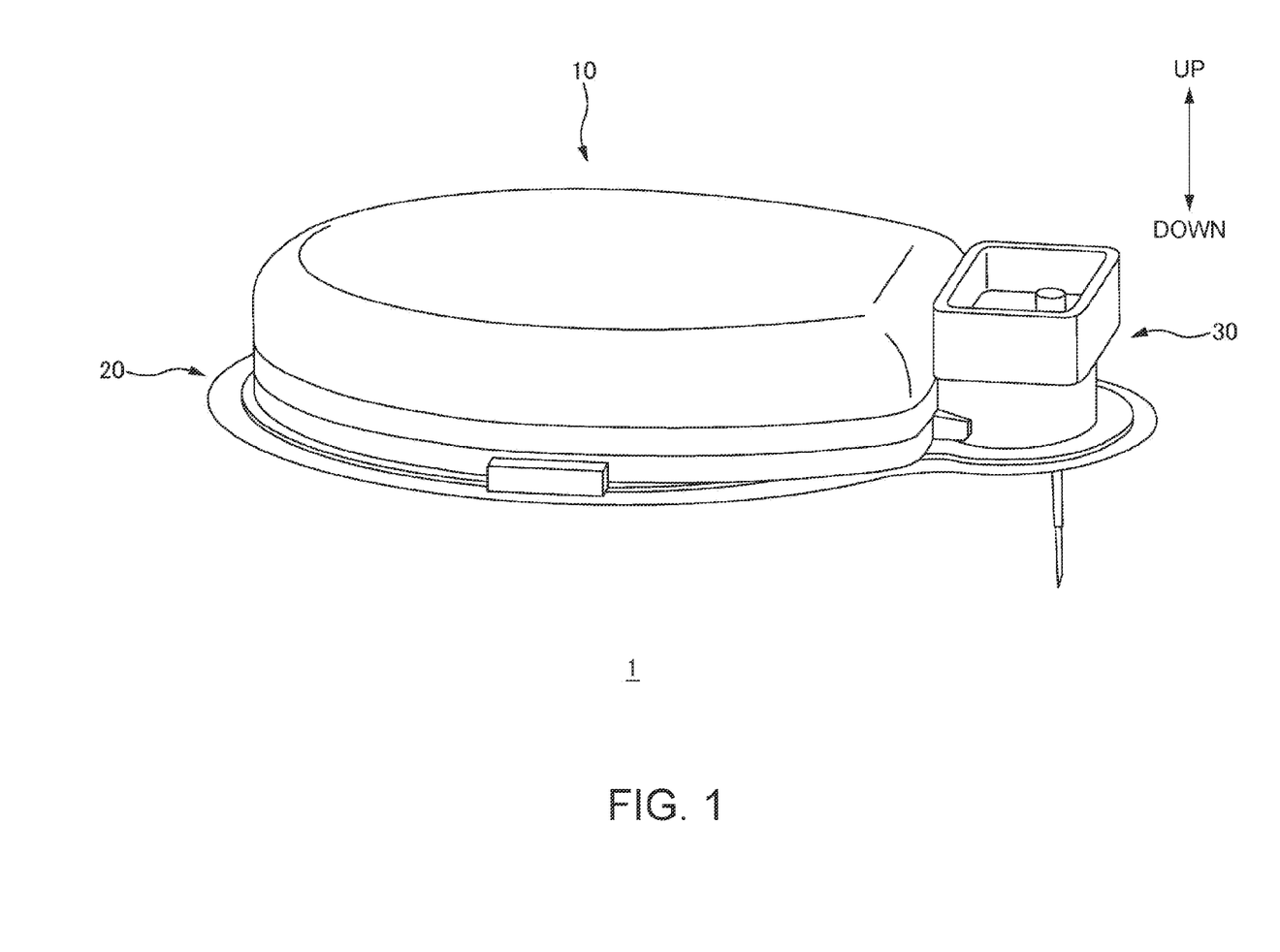
FIG. 1 is a general perspective view of a liquid transporting apparatus.
Figure 2:
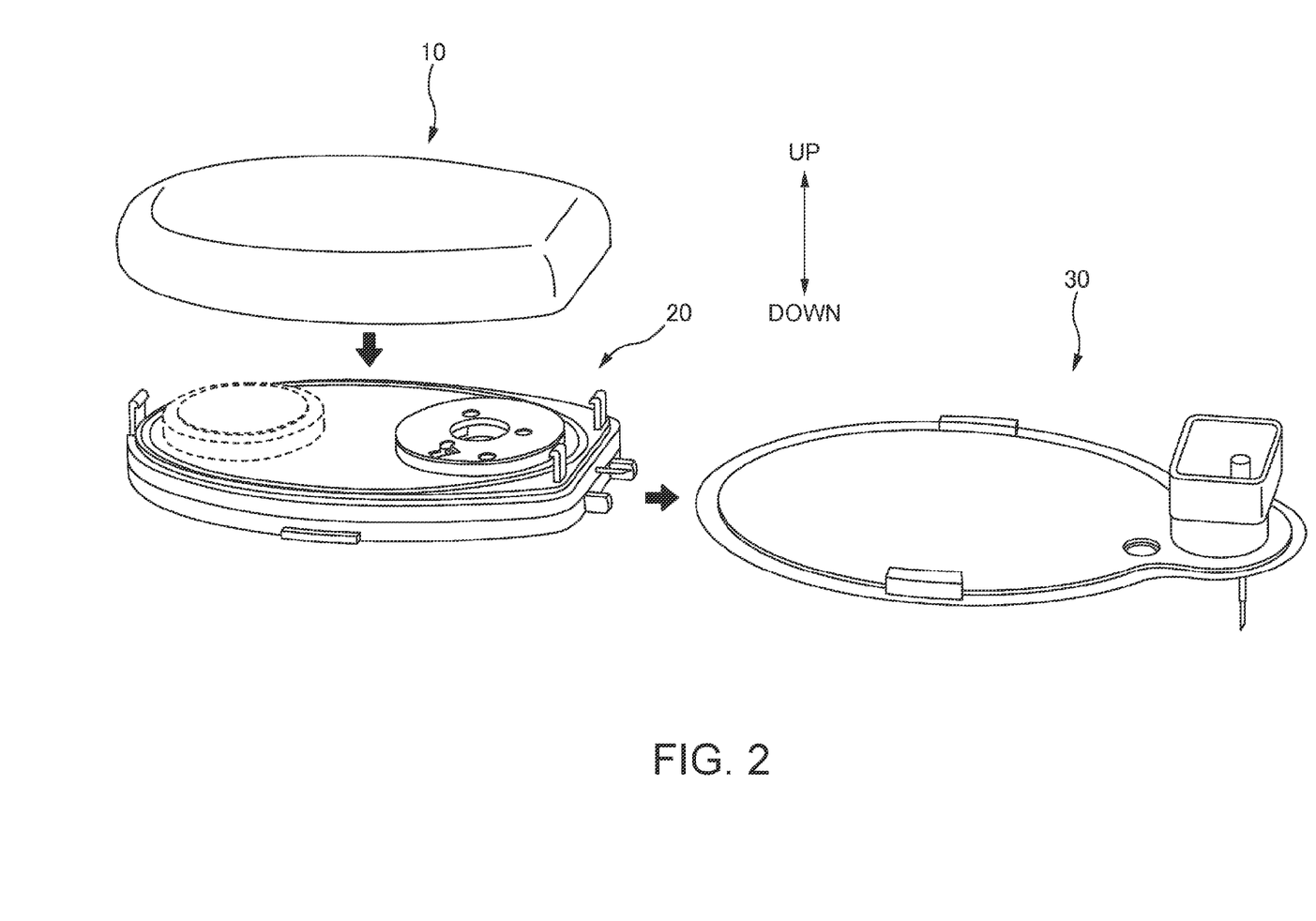
FIG. 2 is an exploded view of the liquid transporting apparatus.

FIG. 1 is a general perspective view of a liquid transporting apparatus 1. FIG. 2 is an exploded view of the liquid transporting apparatus 1. As illustrated in these drawings, a side (biological body side) where the liquid transporting apparatus 1 (which corresponds to the fluid infuser) is adhered is referred to as "down" and an opposite side may be referred to as "up" in the description.

The liquid transporting apparatus 1 is an apparatus configured to transport liquid. The liquid transporting apparatus 1 includes a main body 10, a cartridge 20, and a patch 30. The main body 10, the cartridge 20, and the patch 30 are separable as illustrated in FIG. 2, and are assembled integrally when in use as illustrated in FIG. 1.

The liquid transporting apparatus 1 is preferably used for infusing insulin stored in the cartridge 20 regularly, for example by adhering the patch 30 to the biological body. When the liquid (for example, insulin) stored in the cartridge 20 is finished up, the cartridge 20 is replaced. However, the main body 10 and the patch 30 are continuously used. However, the patch 30 is also replaced at a lower frequency.

Figure 3:
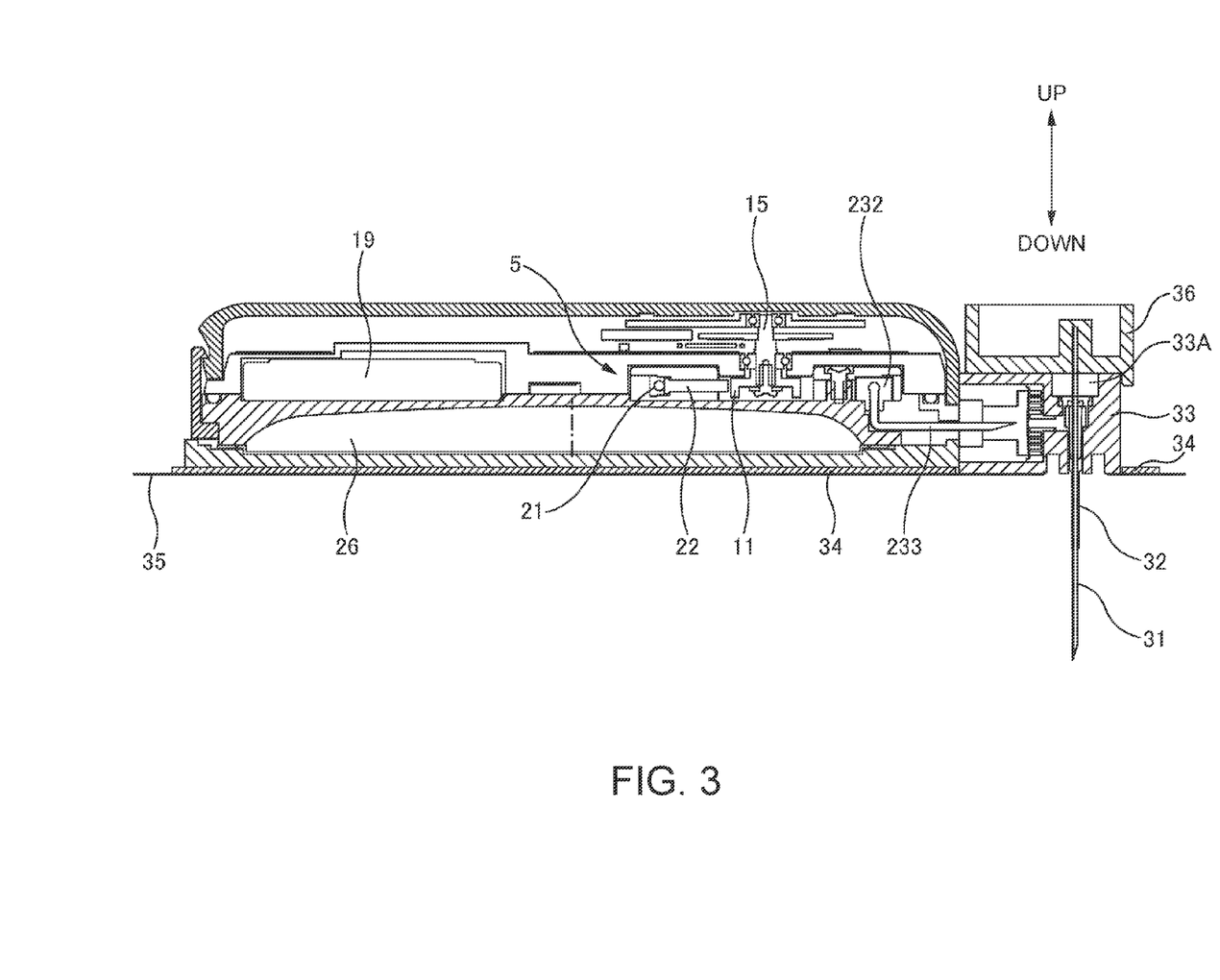
FIG. 3 is a first cross-sectional view of the liquid transporting apparatus.
Figure 4:
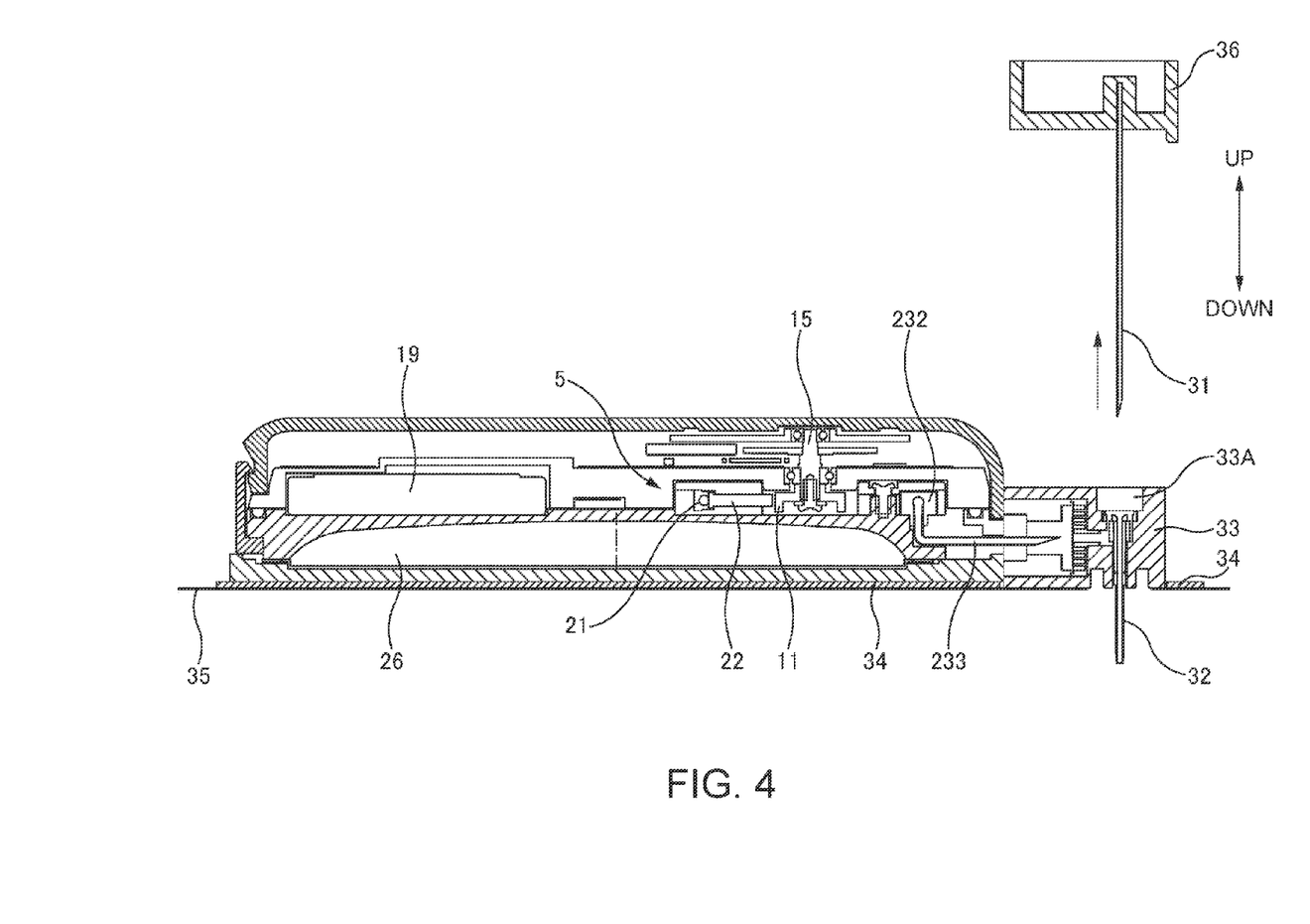
FIG. 4 is a second cross-sectional view of the liquid transporting apparatus.
Figure 5:
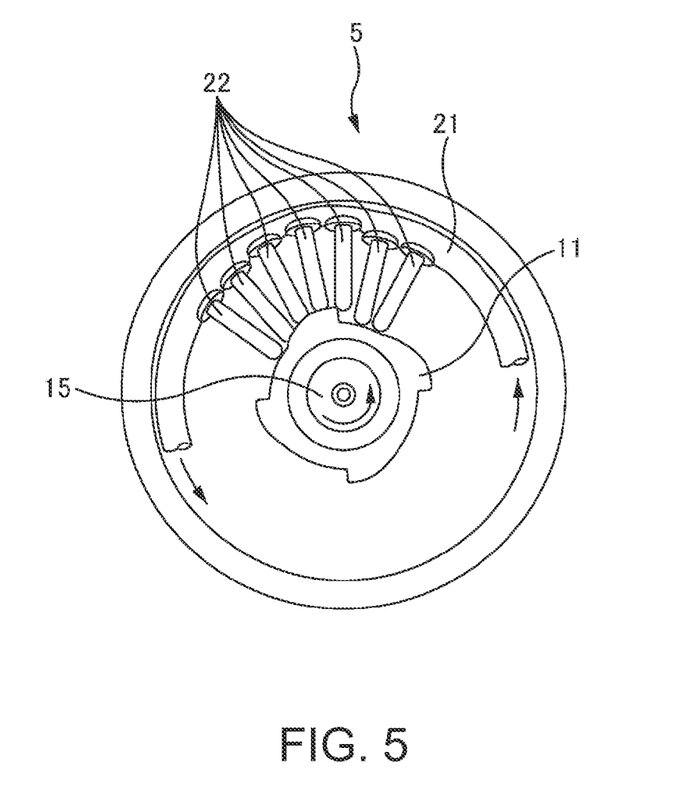
FIG. 5 is a schematic explanatory drawing of a pump unit.

FIG. 3 is a first cross-sectional view of the liquid transporting apparatus 1. FIG. 4 is a second cross-sectional view of the liquid transporting apparatus 1. Both drawings are cross-sectional views when cutting a center of the liquid transporting apparatus 1 in a longitudinal direction of the liquid transporting apparatus 1. FIG. 5 is a schematic explanatory drawing of a pump unit 5. Referring now to FIG. 3 to FIG. 5, an internal structure of the liquid transporting apparatus 1 will be described in brief.

FIG. 3 and FIG. 4 illustrate a rotating shaft 15, a cam 11, and a battery 19 included in the main body 10. A tube 21, fingers 22, and a storage unit 26 included in the cartridge 20 are also illustrated. In addition, an introduction needle 31 included in the patch 30, a soft needle 32 (which corresponds to the infusion tube), a port base 33, a connecting needle septum 33A, an introduction needle septum 33B, a patch base 34, an adhesive pad 35, and an introduction needle holder 36 are also illustrated. The pump unit 5 is also illustrated.

The tube 21 illustrated in FIG. 3 to FIG. 5 is a tube for transporting liquid. An upstream side of the tube 21 communicates with the storage unit 26 of the liquid in the cartridge 20. The tube 21 has a resiliency to an extent to close when pressed by the fingers 22 and restore when the force from the fingers 22 is released.

The fingers 22 are members for closing the tube 21. As illustrated in FIG. 5, the cartridge 20 includes a plurality of fingers 22. The plurality of the fingers 22 are arranged radially from a center of rotation of the cam 11 at regular distance. The plurality of the fingers 22 are arranged between the cam 11 and the tube 21.

The fingers 22 operate so as to follow the cam 11 upon reception of a force therefrom. The fingers 22 each include a rod-shaped shaft portion and a flange-shaped pressing portion. The rod-shaped shaft portion comes into contact with the cam 11, and the flange-shaped pressing portion comes into contact with the tube 21. The fingers 22 are supported so as to be movable along an axial direction.

As illustrated in FIG. 5, the cam 11 includes a plurality of projecting portions on an outer periphery thereof. The fingers 22 are pressed by the projecting portions of the cam 11, so that the tube 21 is closed in sequence. When the fingers 22 come out of contact with the projecting portions, the tube 21 is restored to the original shape by a resiliency of the tube 21.

A motor, which is not illustrated, is rotated by power supplied from the battery 19. When the rotating shaft 15 is rotated, the cam 11 connected thereto is also rotated correspondingly. When the cam 11 is rotated, the plurality of the fingers 22 are pressed in sequence by the projecting portions, and close the tube 21 in sequence from the upstream side in a transporting direction. Accordingly, the tube 21 is caused to perform a peristaltic action, and liquid is compressed and transported to the tube 21. Accordingly, the liquid is supplied toward the patch 30 side via a discharge side joint 232 and a connecting needle 233 (FIG. 3 and FIG. 4).

The patch base 34 illustrated in FIG. 3 and FIG. 4 is a flat panel-shaped member fixed to the port base 33. The adhesive pad 35 is adhered to a bottom surface of the patch base 34. The adhesive pad 35 is an adhesive pad to adhere the patch 30 to the biological body.

An introduction needle septum 33A includes the introduction needle 31 inserted therein. When the introduction needle 31 is pulled out, a hole formed by the introduction needle 31 in the introduction needle septum 33A is spontaneously closed. An area of the port base 33 where the introduction needle 31 is present serves as a flow channel of the liquid after the introduction needle 31 is pulled out.

In a state before usage (FIG. 3), the introduction needle holder 36 is mounted on the port base 33. The introduction needle 31 is inserted into the soft needle 32 and a needle point is exposed from a lower side of the soft needle 32. When adhering the patch 30 to the biological body, the soft needle 32 is picked into the biological body together with the introduction needle 31, and then the introduction needle holder 36 is pulled out from the port base 33 together with the introduction needle 31 (FIG. 4). Accordingly, only the soft needle 32 is indwelt in the subcutaneous structure. Then, the liquid transporting apparatus 1 is operated, so that the liquid in the storage unit 26 is infused into the subcutaneous structure.

Figures 6A, 6B, 6C:
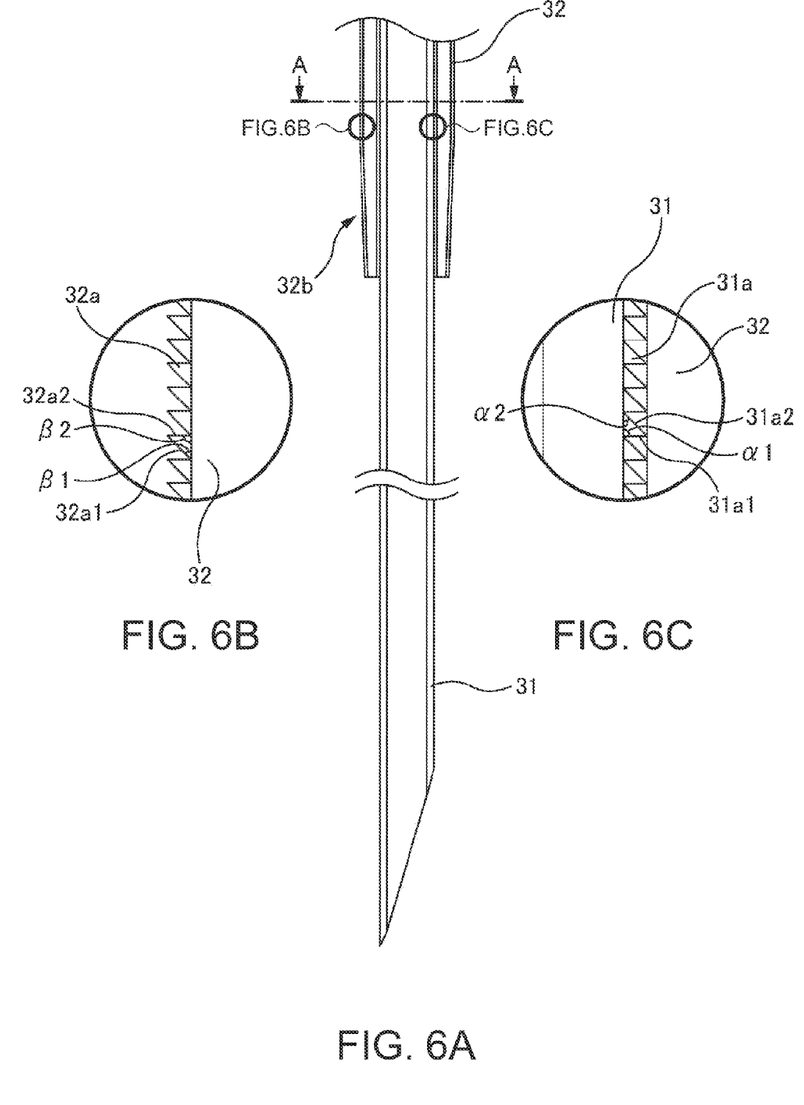
FIGS. 6A-6C are a cross-sectional view of an introduction needle and a soft needle.

FIG. 6 is a cross-sectional view of the introduction needle 31 and the soft needle 32. FIG. 6 illustrates a cross-sectional view taken along a plane passing through a center axis of the introduction needle and the soft needle. FIG. 6 illustrates a partly enlarged drawing of the introduction needle 31 and a partly enlarged drawing of the soft needle 32.

Part of the introduction needle 31 is covered with the soft needle 32. However, the picking end side of the introduction needle 31 is exposed so as to be picked into the biological body or the like. Part of the introduction needle 31 on an outer peripheral surface thereof is provided with a plurality of introduction needle side projections 31*a*. The plurality of introduction needle side projections 31*a* are arranged in a line in the longitudinal direction of the introduction needle 31. The respective introduction needle side projections 31*a* are formed into an umbrella form on the outer periphery of the introduction needle 31. The introduction needle side projections 31*a* is provided within a range covered by the soft needle 32. Accordingly, a portion of the introduction needle 31 coming into contact with the subcutaneous structure when picked is not provided with the projection, so that the introduction needle 31 can be inserted smoothly into the subcutaneous structure or the like.

Each of the introduction needle side projections 31*a* is provided with an introduction needle side first surface 31*a*1 (which corresponds to the first surface) and an introduction needle side second surface 31*a*2 (which corresponds to the second surface). The introduction needle side first surface 31*a*1 is arranged on the picking end side of the introduction needle 31 on each of the introduction needle side projections 31*a*, and the introduction needle side second surface 31*a*2 is arranged on the patch 30 side of each of the introduction needle side projections 31*a*.

The introduction needle side first surface 31*a*1 includes an angle of inclination with respect to the longitudinal direction of the introduction needle 31, and the angle of inclination (the angle of inclination on the side where the introduction needle side projections 31*a* is present) is illustrated as an introduction needle side first angle of inclination $\alpha 1$ (which corresponds to the angle of inclination of the first surface). The introduction needle side second surface 31*a*2 also includes an angle of inclination with respect to the longitudinal direction of the introduction needle 31, and the angle of inclination (the angle of inclination on the side where the introduction needle side projections 31*a* is present) is illustrated as an introduction needle side second angle of inclination $\alpha 2$ (which corresponds to the angle of inclination of the second surface).

The introduction needle side first angle of inclination $\alpha 1$ is larger than the introduction needle side second angle of inclination $\alpha 2$. Preferably, the introduction needle side first angle of inclination $\alpha 1$ has an angle of inclination of 90 degrees or more. Therefore, the introduction needle side first surface 31*a*1 of the introduction needle side projections 31*a* is configured to engage an inner peripheral surface of the soft needle 32 easily. Then, the introduction needle side projections 31*a* allows the soft needle 32 to be inserted into the subcutaneous structure by adequately supporting the soft needle 32 from the inner peripheral surface of the soft needle 32.

The introduction needle side second angle of inclination $\alpha 2$ is smaller than the introduction needle side first angle of inclination $\alpha 1$. Therefore, the frictional force of the introduction needle 31 with respect to the soft needle 32 in the pulling-out direction is smaller than that in the opposite direction. In other words, the introduction needle 31 may be pulled out easily from the soft needle 32.

In contrast, a plurality of soft needle side projections 32*a* are provided on an outer peripheral surface of the soft needle 32. The plurality of the soft needle side projections 32*a* are arranged in a line in the longitudinal direction of the soft needle 32. The respective soft needle side projections 32*a* are formed into an umbrella shape on an outer periphery of the soft needle 32.

Each of the soft needle side projections 32*a* is provided with a soft needle side first surface 32*a*1 (which corresponds to the third surface) and a soft needle side second surface 32*a*2 (which corresponds to the fourth surface). The soft needle side first surface 32*a*1 of the soft needle side projections 32*a* is arranged on a distal end side of the soft needle 32, and the soft needle side second surface 32*a*2 of the soft needle 32 is arranged on the patch 30 side.

The soft needle side first surface 32*a*1 has an angle of inclination with respect to the longitudinal direction of the soft needle 32, and the angle of inclination (the angle of inclination on the side where the soft needle side projections 32*a* is present) is illustrated as a soft needle side first angle of inclination $\beta 1$ (which corresponds to the angle of inclination of the third surface). The soft needle side second surface 32*a*2 has an angle of inclination with respect to the longitudinal direction of the soft needle 32, and the angle of inclination (the angle of inclination on the side where the soft needle side projections 32*a* is present) is illustrated as a soft needle side second angle of inclination $\beta 2$ (which corresponds to the angle of inclination of the fourth surface).

The soft needle side first angle of inclination $\beta 1$ is smaller than the soft needle side second angle of inclination $\beta 2$. With the provision of the angles of inclination as described above, the frictional force of the soft needle 32 with respect to the subcutaneous structure is smaller in the direction of insertion than that in the opposite direction. In other words, the soft needle 32 may be inserted easily into the subcutaneous structure.

The soft needle side second angle of inclination $\beta 2$ of the soft needle 32 is larger than the soft needle side first angle of inclination $\beta 1$, so that the soft needle side projections 32*a* engages easily with the subcutaneous structure and can hardly be pulled out from the subcutaneous structure to some extent. However, when pulling out the soft needle 32 from the subcutaneous structure, the introduction needle 31 is in a state of being already pulled out from the soft needle 32. Therefore, since soft needle 32 is deformable inward by a resilient force thereof, the soft needle 32 may be pulled out without applying a burden on the biological body irrespective of the soft needle side projections 32*a* provided on the outer peripheral surface.

The soft needle 32 includes a tapered portion 32*b* configured to be reduced in thickness at a distal end portion thereof as illustrated in FIG. 6. With the tapered shape, picking of the soft needle 32 into the biological body or the like is facilitated.

Figure 7:
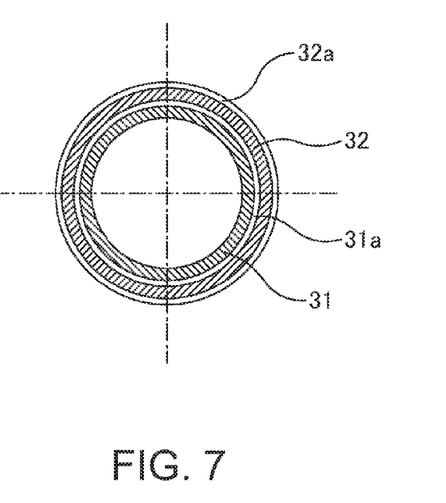
FIG. 7 is a cross-sectional view of FIG. 6A of a first embodiment taken along a line A-A.

FIG. 7 is a cross-sectional view of FIG. 6 of a first embodiment taken along a line A-A. In FIG. 7, the introduction needle 31 and the soft needle 32 are illustrated. FIG.

7 also illustrates the introduction needle side projections 31a projecting from an outer peripheral surface of the introduction needle 31 and a soft needle side projections 32a projecting from the outer peripheral surface of the soft needle 32.

As illustrated in FIG. 7, the introduction needle side second surface 31a2 may have a shape that matches the shape of the introduction needle side first surface 31a1 of the introduction needle side projections 31a. In the same manner, the soft needle side second surface 32a2 may have a shape that matches the shape of the soft needle side first surface 32a1 of the soft needle side projections 32a.

The introduction needle 31 is preferably formed of a metal. The introduction needle side projections 31a on the outer peripheral surface of the introduction needle 31 may be molded by a cold forging process which rotates the introduction needle 31 while pressing against a metal die curved with the shape of the introduction needle side projections 31a.

The soft needle 32, which is softer than the introduction needle, is preferably formed of a resin. The soft needle side projections 32a on the peripheral surface of the soft needle 32 may be formed by balloon molding process by pouring the melt resin in the metal die having the shape of the soft needle side projections 32a curved therein, and infusing air from the inside.

Figure 8:
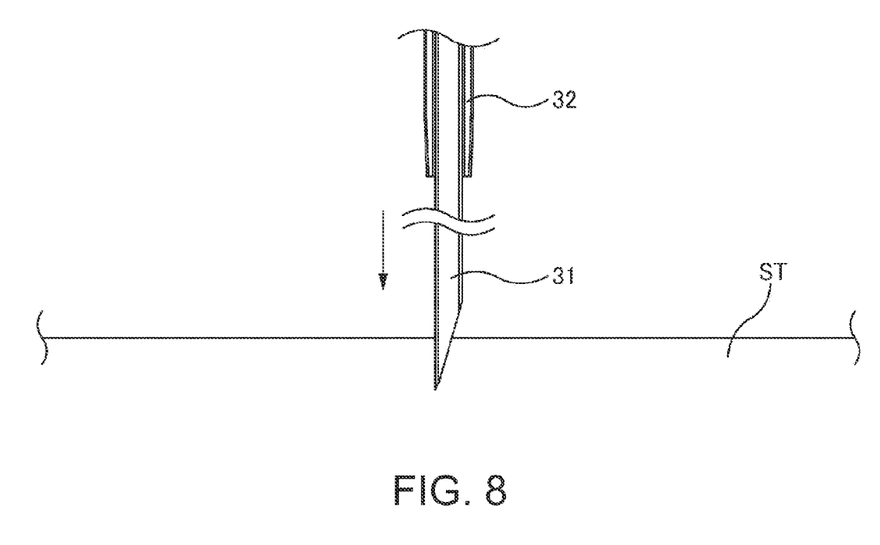
FIG. 8 is a first explanatory drawing of an insertion of the soft needle.
Figure 9:
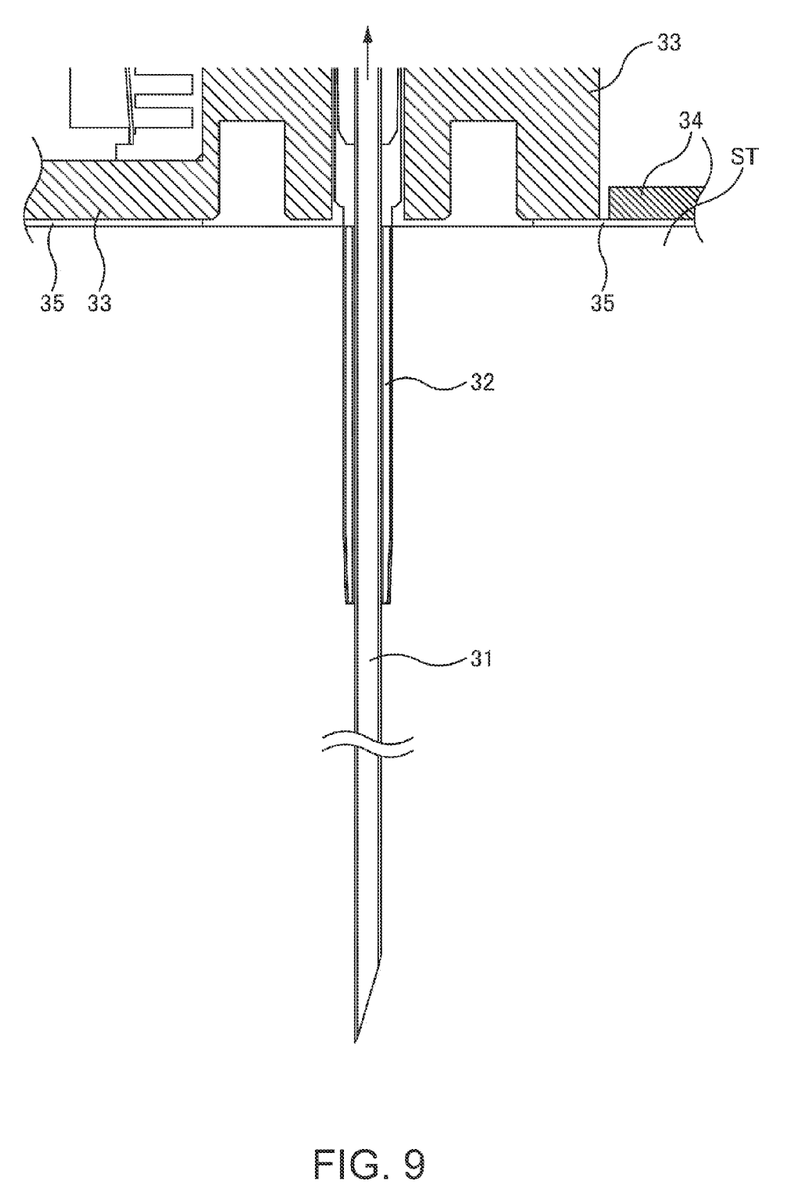
FIG. 9 is a second explanatory drawing of an insertion of the soft needle.
Figure 10:
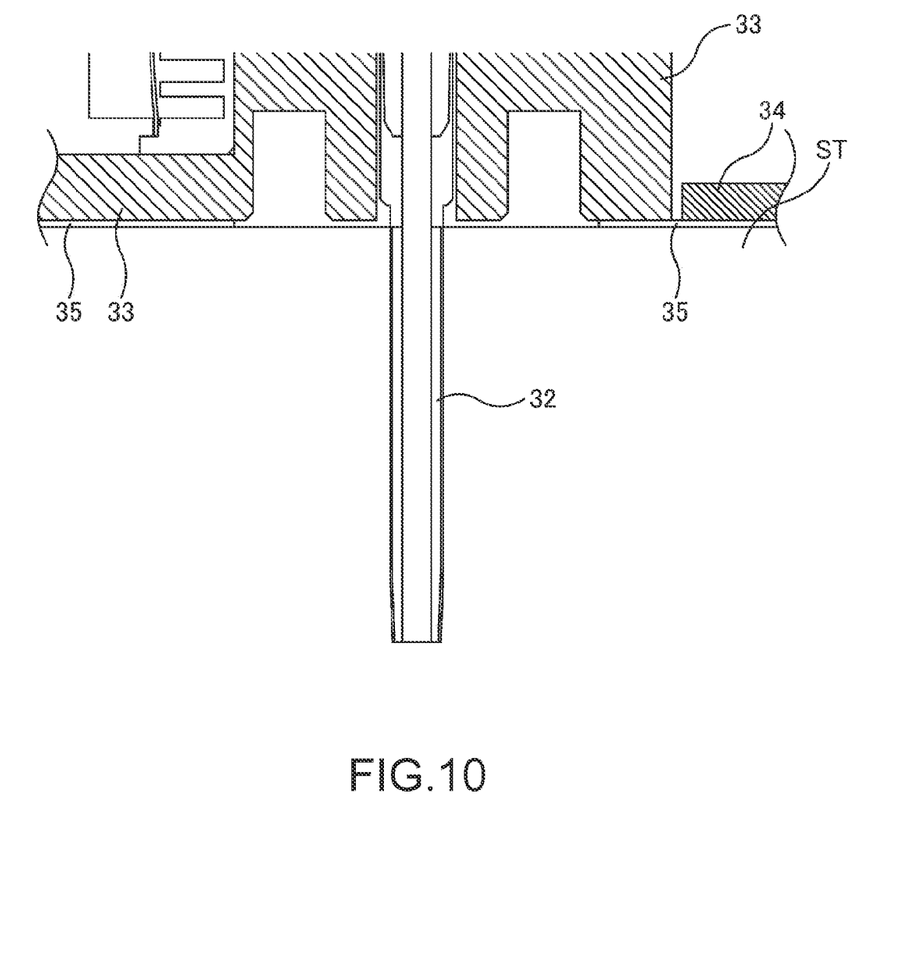
FIG. 10 is a third explanatory drawing of an insertion of the soft needle.

FIG. 8 is a first explanatory drawing of an insertion of the soft needle 32. FIG. 9 is a second explanatory drawing of an insertion of the soft needle 32. FIG. 10 is a third explanatory drawing of an insertion of the soft needle 32. Referring now to these drawings, a procedure of picking and indwelling the soft needle 32 in the subcutaneous structure of the first embodiment will be described.

As illustrated in FIG. 8, the introduction needle 31 and the soft needle 32 proceed integrally in a direction substantially vertical to a subcutaneous structure ST. Then, the introduction needle 31 picks the subcutaneous structure ST. Subsequently, the introduction needle 31 and the soft needle 32 integrally proceed toward the subcutaneous structure, whereby the soft needle 32 is also picked into the subcutaneous structure ST.

The introduction needle 31 and the soft needle 32 are picked into the subcutaneous structure ST until the adhesive pad 35 comes into contact with a skin surface as illustrated in FIG. 9. The adhesive pad 35 has an adhesiveness, and hence the liquid transporting apparatus 1 is adhered to the skin.

Subsequently, the introduction needle holder 36 is pulled out. A rear end of the introduction needle 31 is fixed to the introduction needle holder 36. Therefore, when the introduction needle holder 36 is pulled out, the introduction needle 31 is pulled out from the subcutaneous structure ST correspondingly. As illustrated in FIG. 10, only the soft needle 32 is indwelt in the subcutaneous structure ST.

In this manner, after only the soft needle 32 is indwelt in the subcutaneous structure ST, liquid such as insulin, for example, may be administered into the subcutaneous structure via the interior of the soft needle 32.

As described above, when picking the soft needle 32 into the subcutaneous structure, the introduction needle side first surface 31a1 of the introduction needle side projections 31a of the introduction needle 31 can easily engage an inner peripheral surface of the soft needle 32. Therefore, the introduction needle side projections 31a allows the soft needle 32 to be inserted into the subcutaneous structure by adequately supporting the soft needle 32 from the inner peripheral surface of the soft needle 32.

When the introduction needle 31 is pulled out described above, since the introduction needle 31 is provided with the introduction needle side projections 31a configured to reduce the frictional force with respect to the soft needle 32, the introduction needle 31 may be pulled out with a smaller force in comparison with those which are not provided with the introduction needle side projections 31a.

Since the soft needle 32 includes the soft needle side projections 32a configured to reduce the frictional force in a direction of picking with respect to the subcutaneous structure ST, the soft needle 32 may be picked into the subcutaneous structure ST with a force lighter than those which are not provided with the soft needle side projections 32a. After having been picked, the soft needle 32 may be prevented from coming away from the subcutaneous structure ST to some extent. In contrast, since soft needle 32 is deformable inward by a resilient force of the soft needle 32 itself, the soft needle 32 may be pulled out from the biological body without applying a burden on the biological body.

Second Embodiment

Figure 11:
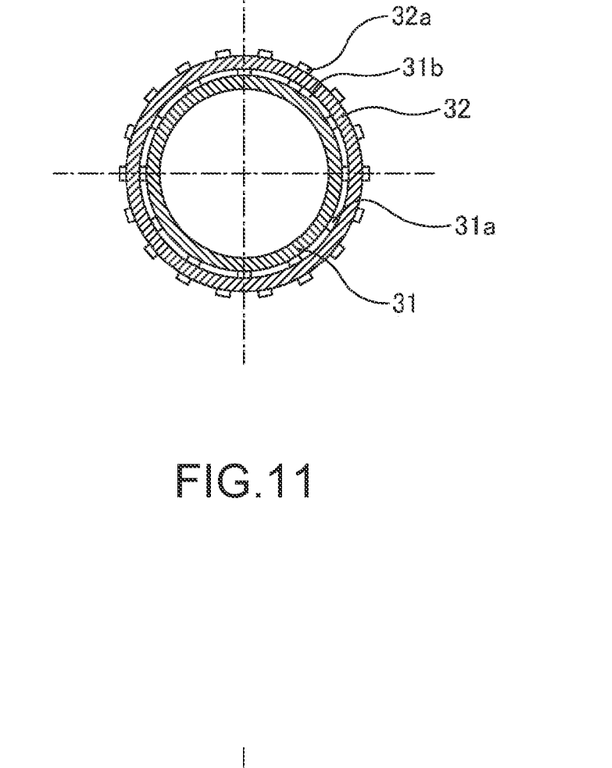
FIG. 11 is a cross-sectional view of FIG. 6A of a second embodiment taken along a line A-A.

FIG. 11 is a cross-sectional view of FIG. 6 of a second embodiment taken along a line A-A. In FIG. 11, the introduction needle 31 and the soft needle 32 in the second embodiment are illustrated. The second embodiment is different from the first embodiment in that the plurality of the introduction needle side projections 31a are arranged at predetermined intervals on the outer peripheral surface of the introduction needle 31, and a groove 31b is formed so as to extend between the introduction needle side projections 31a in the longitudinal direction of the introduction needle 31.

In this manner, in the second embodiment, since the groove 31b is provided between the introduction needle side projections 31a, a contact area between the outer peripheral surface of the introduction needle 31 and the inner peripheral surface of the soft needle 32 may be reduced. Therefore, the frictional force generated therebetween may be reduced. Therefore, the introduction needle 31 can be pulled from the soft needle 32 easily. In addition, by adjusting the width of the groove 31b, a degree of ease of pulling out may be adjusted.

Third Embodiment

Figure 12:
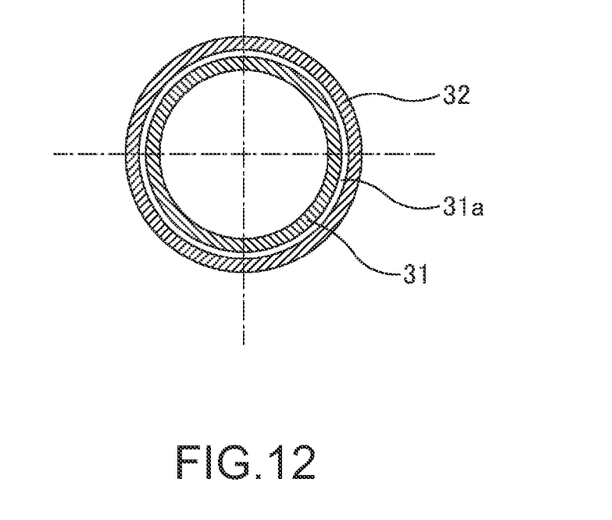
FIG. 12 is a cross-sectional view of FIG. 6A of a third embodiment taken along a line A-A.

FIG. 12 is a cross-sectional view of FIG. 6 of a third embodiment taken along a line A-A. In FIG. 12, the introduction needle 31 and the soft needle 32 in the third embodiment are illustrated. The third embodiment is different from the first embodiment in that the soft needle side projections 32a are not provided on the outer peripheral surface of the soft needle 32.

In this mode as well, since the introduction needle side projections 31a are configured to engage the inner peripheral surface of the soft needle 32 easily, the introduction needle side projections 31a allow the soft needle 32 to be inserted into the subcutaneous structure by adequately supporting the soft needle 32 from the inner peripheral surface of the soft needle 32. The groove 31b as described in conjunction with the second embodiment may be provided between the introduction needle side projections 31a.

OTHER EMBODIMENTS

The embodiment described above is for facilitating the understanding of the invention, and is not for interpreting the invention in a limited range. It is needless to say that the invention may be modified or improved without departing from the scope of the invention and equivalents are included in the invention.

The entire disclosure of Japanese Patent Application No. 2013-219894, filed Oct. 23, 2013 is expressly incorporated by reference herein.

What is claimed is:

1. A fluid infuser comprising:

an introduction needle having a projection on a peripheral surface; and an infusion tube configured to cover the introduction needle, wherein the projection of the introduction needle is installed at a position where the introduction needle comes into contact with the infusion tube, and includes a first surface and a second surface, wherein the first surface is arranged at a picking end side of the introduction needle with respect to the second surface, and an angle of inclination of the first surface is larger than an angle of inclination of the second surface, a projection is provided on an outer peripheral surface of the infusion tube, the projection of the infusion tube includes a third surface and a fourth surface, an angle of inclination of the third surface is smaller than an angle of inclination of the fourth surface, the third surface is arranged on an inlet port side of the infusion tube, and the projection of the infusion tube has an opposite inclination as the projection of the introduction needle.

2. The fluid infuser according to claim 1, wherein the projection of the introduction needle is provided in a range where the infusion tube covers the introduction needle.

3. The fluid infuser according to claim 1, further comprising:

a groove extending in a longitudinal direction of the introduction needle in an outer periphery of the introduction needle.

4. The fluid infuser according to claim 1, wherein a material of the introduction needle is harder than the material of the infusion tube.

5. The fluid infuser according to claim 1, wherein a material of the introduction needle is a metal, and a material of the infusion tube is a resin.

6. The fluid infuser according to claim 1, wherein the angle of inclination of the first surface is 90 degrees or more.

7. The fluid infuser according to claim 1, wherein an outer peripheral length of the infusion tube on the inlet port side is shorter than an outer peripheral length of the infusion tube on the other end side.

* * * * *